US009588260B2

(12) United States Patent
Koizumi

(10) Patent No.: US 9,588,260 B2
(45) Date of Patent: Mar. 7, 2017

(54) MICROLENS SUBSTRATE AND IMAGING APPARATUS

(71) Applicant: Eichi Koizumi, Kanagawa (JP)

(72) Inventor: Eichi Koizumi, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 15/071,322

(22) Filed: Mar. 16, 2016

(65) Prior Publication Data

US 2016/0274277 A1    Sep. 22, 2016

(30) Foreign Application Priority Data

Mar. 20, 2015 (JP) ................................ 2015-058573

(51) Int. Cl.

| G02B 27/10 | (2006.01) |
|---|---|
| G02B 7/02 | (2006.01) |
| G02B 3/00 | (2006.01) |
| A61B 1/05 | (2006.01) |
| H04N 5/225 | (2006.01) |

(52) U.S. Cl.
CPC ............ *G02B 3/0075* (2013.01); *A61B 1/051* (2013.01); *G02B 3/0006* (2013.01); *G02B 7/028* (2013.01); *G02B 27/1013* (2013.01); *G02B 27/1066* (2013.01); *H04N 5/2253* (2013.01);
(Continued)

(58) Field of Classification Search
CPC .. G02B 3/0006; G02B 3/0037; G02B 3/0056; G02B 3/0075; G02B 7/021; G02B 7/023; G02B 7/028; G02B 7/10; G02B 27/10; G02B 27/1013; G02B 27/102; G02B 27/1066; H04N 5/2253–5/2255; H04N 5/369; A61B 1/00163; A61B 1/05; A61B 1/051; G03B 5/00
USPC ............... 359/513, 557, 619, 811, 819, 820; 348/76, E5.027, 208.7, 208.99, 240.99, 348/374, 375; 361/728, 809
See application file for complete search history.

(56) References Cited

U.S. PATENT DOCUMENTS

| 5,920,061 A * | 7/1999 | Feng ................... G06K 7/10722 |
|---|---|---|
| | | 235/462.42 |
| 6,669,093 B1 * | 12/2003 | Meyerson ................ G06K 7/12 |
| | | 235/462.45 |

(Continued)

FOREIGN PATENT DOCUMENTS

| JP | 2013-109011 | 6/2013 |
|---|---|---|
| JP | 2015-17834 | 1/2015 |

*Primary Examiner* — Loha Ben
(74) *Attorney, Agent, or Firm* — Oblon, McClelland, Maier & Neustadt, L.L.P.

(57) ABSTRACT

A microlens substrate includes a light receiving section that includes a light receiving surface configured to receive light, a supporting member that fixes the light receiving section, a microlens array that includes a plurality of microlenses configured to guide the light to the light receiving section, a lens holding member that holds the microlens array, and a fixing member that fixes the supporting member and the lens holding member. The fixing member includes a first fixing part that fixes the lens holding member and a second fixing member that fixes the supporting member. The lens holding member includes a lens holding part that holds the microlens array. The lens holding part is disposed at a position between the first fixing part and the second fixing part in a direction orthogonal to the light receiving surface.

6 Claims, 7 Drawing Sheets

(52) U.S. Cl.
CPC ......... *H04N 5/2254* (2013.01); *G02B 3/0056* (2013.01); *G02B 7/023* (2013.01); *G02B 27/102* (2013.01)

(56) References Cited

U.S. PATENT DOCUMENTS

| | | | | |
|---|---|---|---|---|
| 7,872,780 | B2 * | 1/2011 | Nomura | G03B 3/04 |
| | | | | 358/474 |
| 8,587,718 | B2 * | 11/2013 | Ichimura | H04N 5/2254 |
| | | | | 348/375 |
| 8,680,669 | B2 * | 3/2014 | Kurihara | B23K 1/0016 |
| | | | | 257/704 |
| 2013/0128092 | A1 | 5/2013 | Ogasahara et al. | |
| 2014/0078280 | A1 * | 3/2014 | Yoshida | A61B 1/00163 |
| | | | | 348/76 |
| 2016/0062110 | A1 * | 3/2016 | Kashima | G02B 7/021 |
| | | | | 359/513 |

* cited by examiner

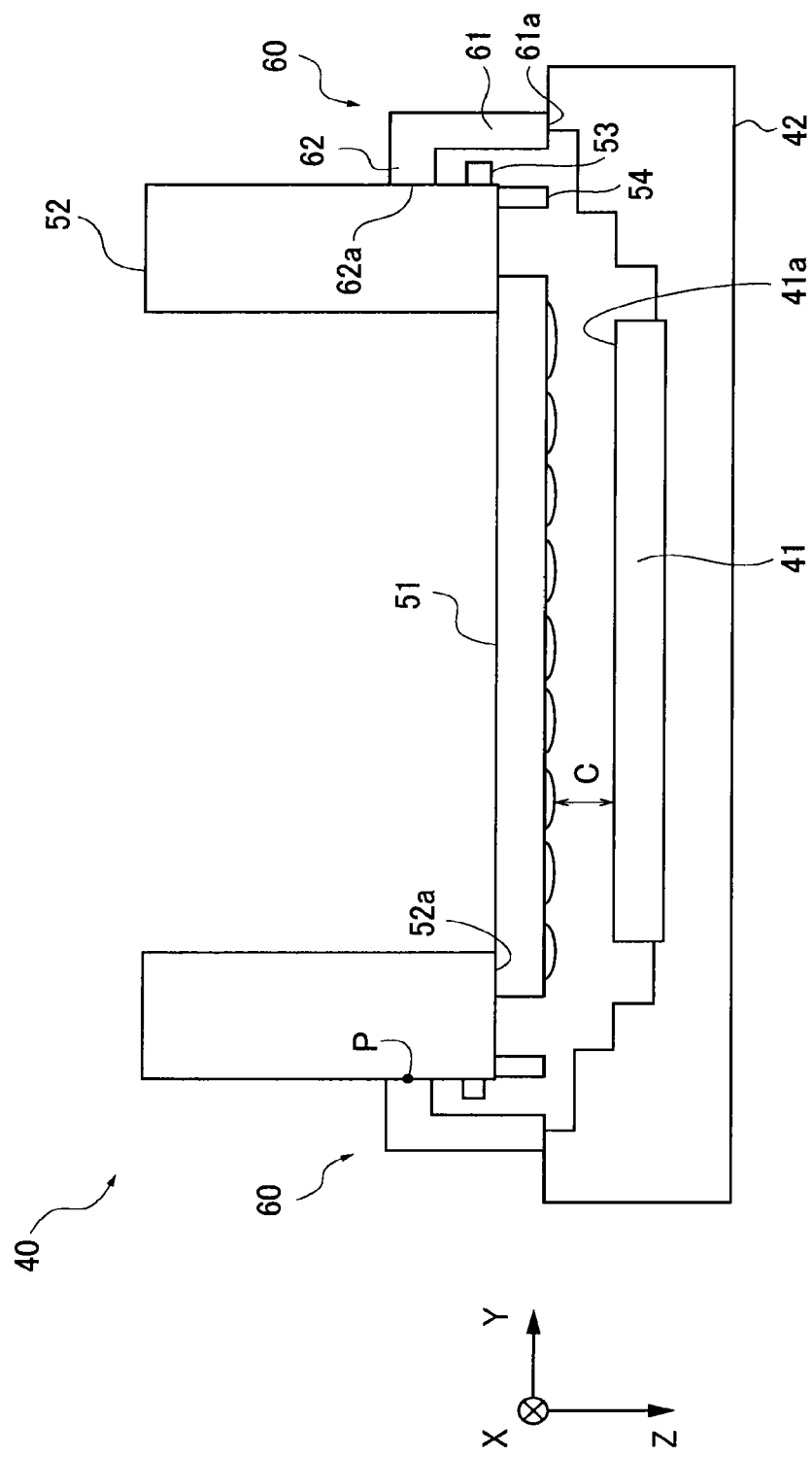

MICROLENS SUBSTRATE AND IMAGING APPARATUS

CROSS-REFERENCE TO RELATED APPLICATION

The present application is based on and claims priority to Japanese patent application No. 2015-058573, filed on Mar. 20, 2015, the disclosure of which is hereby incorporated by reference herein in its entirety.

BACKGROUND

Technical Field

The disclosure relates to a microlens substrate and an imaging apparatus including the microlens substrate.

Description of Related Art

An imaging apparatus including a microlens array in front of an image pickup element is taught by, for example, Patent Literature 1 (JP2015-017834 A). The imaging apparatus of Patent Literature 1 simultaneously projects, on the image pickup element, images of an object from a plurality of viewpoints. With this, the imaging apparatus of Patent Literature 1 estimates a distance to the object and reconstructs a two-dimensional image by stitching images.

Patent Literature 2 (JP2013-109011 A) discloses a camera module that achieves high accuracy positioning with a compound-eye structure. The camera module of Patent Literature 2 obtains a high quality image from an image group photographed by using the compound-eye structure.

SUMMARY

However, in the configurations of Patent Literatures 1 and 2, a distance between the microlens array and image pickup element may be changed due to expansion and compression of the elements caused by temperature changes.

In view of the above, an object of this disclosure is to provide a microlens substrate that reduces a variation of a distance between a microlens array and an image pickup element caused by thermal expansion and thermal compression.

To achieve the above object, an aspect of the disclosure provides a microlens substrate including a light receiving section that includes a light receiving surface configured to receive light, a supporting member that fixes the light receiving section, a microlens array that includes a plurality of microlenses configured to guide the light to the light receiving section, a lens holding member that holds the microlens array, and a fixing member that fixes the supporting member and the lens holding member. The fixing member includes a first fixing part that fixes the lens holding member and a second fixing member that fixes the supporting member. The lens holding member includes a lens holding part that holds the microlenses array, and the lens holding part is disposed at a position between the first fixing part and the second fixing part in a direction orthogonal to the light receiving surface.

BRIEF DESCRIPTION OF DRAWINGS

FIG. 3 is a view illustrating an example of a configuration of a microlens substrate according to the first embodiment;

DETAILED DESCRIPTION

First Embodiment

Figure 1:
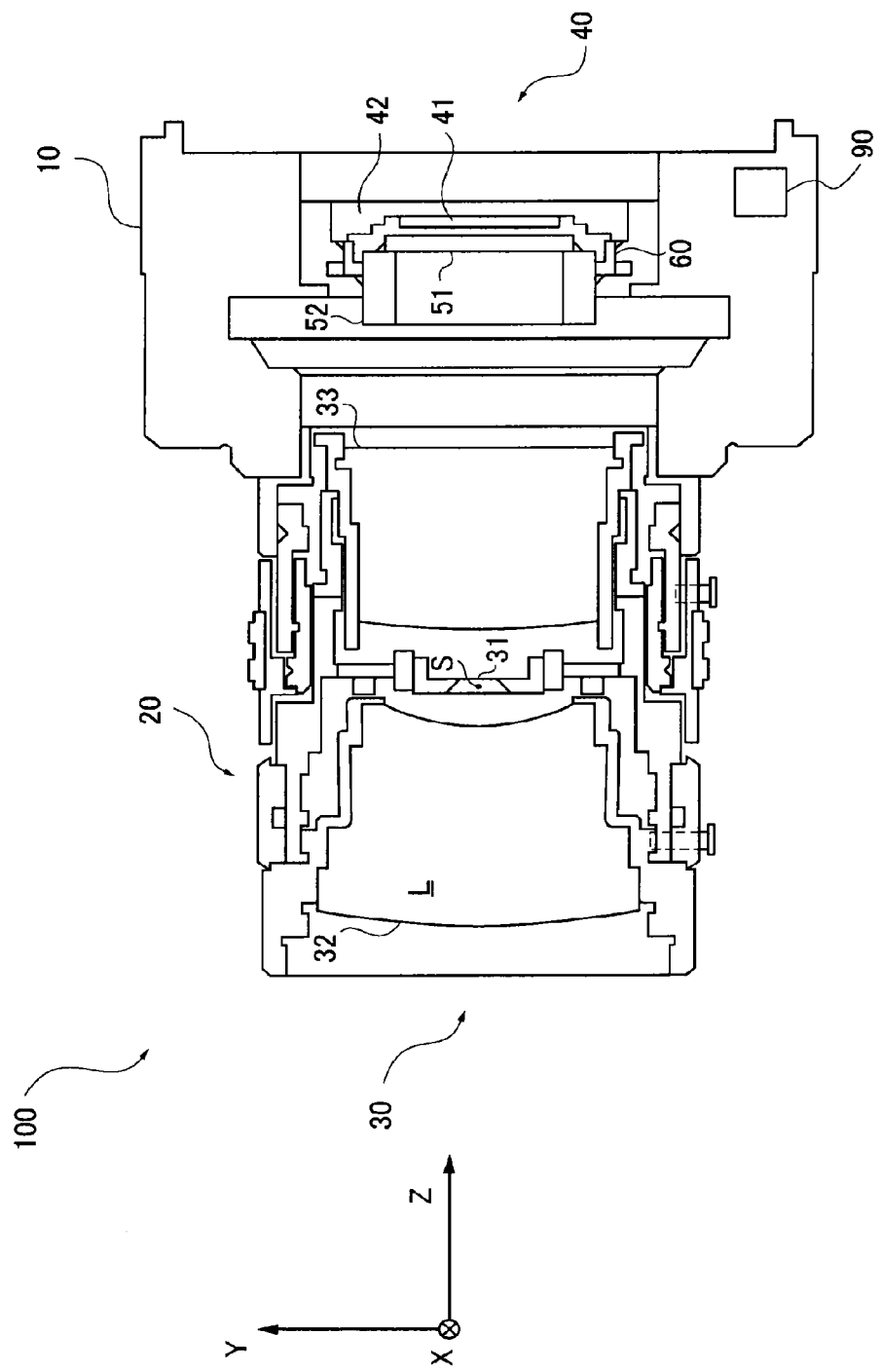
FIG. 1 is a cross-sectional view illustrating an example of an overall configuration of an imaging apparatus according to a first embodiment.

As illustrated in FIG. 1, a color measuring camera (an imaging apparatus of a first embodiment) 100 includes a plurality of lenses L, a lens barrel 20 to hold the lenses L, and a housing (body) 10 to hold the lens barrel 20. The plurality of lenses L configures an imaging optical system 30 to capture luminous flux from an object. Hereinafter, in this embodiment, a direction parallel to an optical axis of the imaging optical system 30 is referred to as Z direction, a vertical direction in FIG. 1 as Y direction, and a direction orthogonal to both the Z direction and Y direction as X direction. The color measuring camera 100 further includes an image pickup element (light receiving section) 41 and a microlens 51. The image pickup element 41 receives light transmitted through the imaging optical system 30 and converts the light into image information. The microlens 51 is disposed on the upstream side of the image pickup element 41 in Z direction such that the images of the object are projected onto the image pickup element 41 from a plurality of viewpoints. The color measuring camera 100 also includes a supporting member 42, a lens holding member 52, and an adjuster (fixing member) 60. The supporting member 42 fixes the image pickup element 41 to the housing 10. The lens holding member 52 holds the microlens 51. The adjuster 60 abuts to the lens holding member 52 and supporting member 42 so as to determine and fix the positions thereof. The color measuring camera 100 further includes a controller (processor) 90 to control each section.

The image pickup element 41, the microlens 51, the lens holding member 52, and the adjuster 60 configure a microlens unit (microlens substrate) 40 that is removable from the housing 10. Note that FIG. 1 illustrates a cross-sectional view of YZ plane. As illustrated in the following drawings, the microlens unit 40 of this embodiment has substantially a square shape in view from Z direction. However, this is only an example. For instance, the microlens unit may have a rotation symmetric shape around Z axis.

Figure 2:
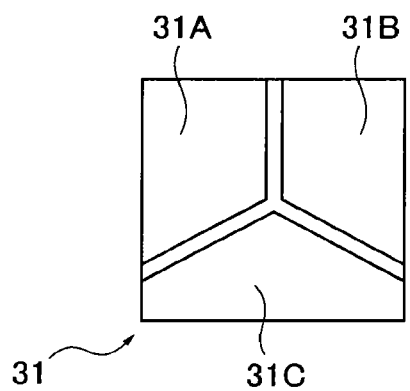
FIG. 2 is a view illustrating an example of a configuration of an optical filter according to the first embodiment.

As illustrated in FIG. 2, the imaging optical system 30 includes an optical filter 31. The optical filter 31 is formed by radially combining color filters 31A, 31B, 31C. Each color filter 31A, 31B, 31C transmits light in a predetermined frequency range. As illustrated in FIG. 1, the imaging optical system 30 includes a front lens group 32 and a rear lens group 33. The front lens group 32 is disposed on the upstream side of the optical filter 31 in Z direction, i.e., disposed on −Z direction side with respect to the optical filter 31. The rear lens group 33 is disposed on +Z direction side with respect to the optical filter 31. The optical filter 31 is preferably disposed in the vicinity of an aperture of the imaging optical system 30. In the embodiment, the vicinity of the aperture means any position in an area determined in accordance with an optical design and includes the position of the aperture stop S. Note that the optical filter 31 may be formed by adhering the color filters 31A, 31B, 31C, or may be formed by dividing a region of a transparent member (e.g., a glass) and by vapor-depositing the color filters 31A, 31B, 31C to each divided region.

The lens barrel 20 has a cylindrical shape and supports the lenses L and the optical filter 31. The lens barrel 20 is fixed to the housing 10.

A configuration of the microlens unit 40 will be explained. As described above and as illustrated in FIG. 3, the microlens unit 40 includes the image pickup element 41, the microlens 51, the lens holding member 52, and the adjuster 60. The image pickup element 41 includes a light receiving surface 41a being perpendicular to the Z direction so as to receive the luminous flux incident thereto.

Figure 4A:
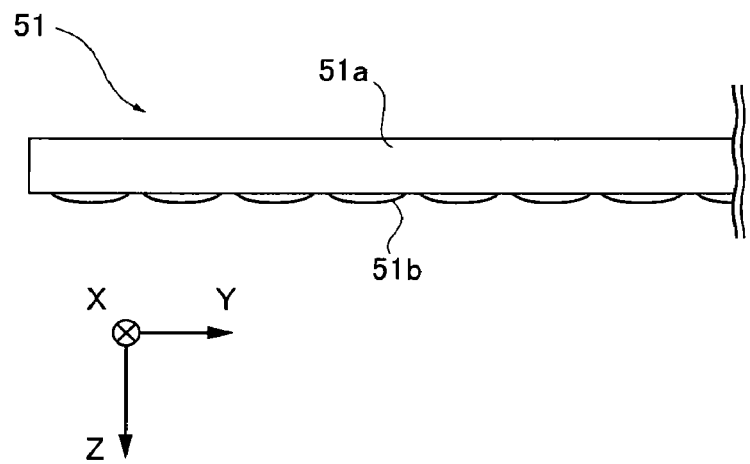
FIG. 4A is a view illustrating an example of a configuration of a microlens array according to the first embodiment.
Figure 4B:
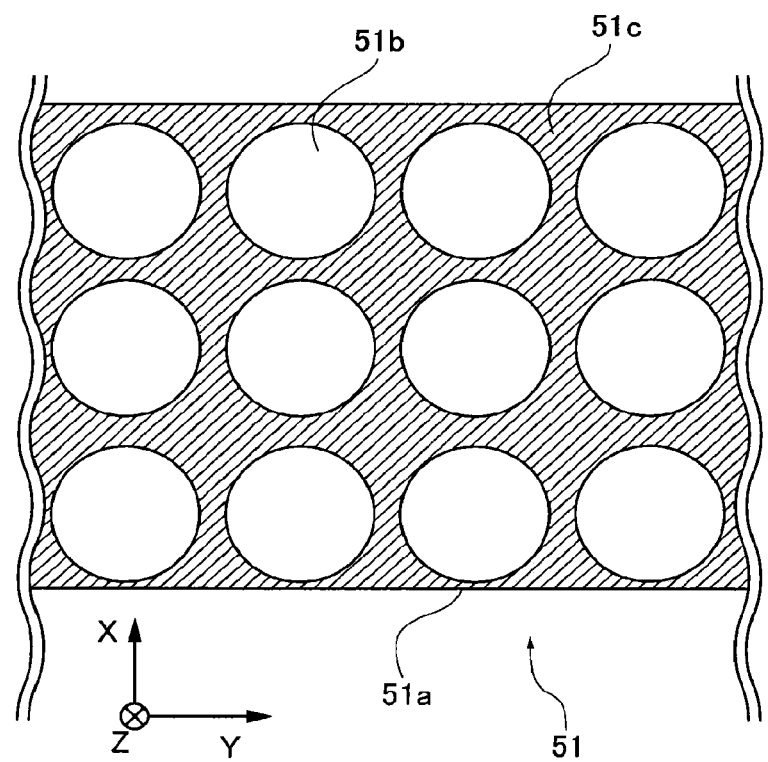
FIG. 4B is another view illustrating the example of the configuration of the microlens array according to the first embodiment.

As illustrated in FIG. 4A, the microlens 51 includes a transparent glass plate member 51a and a plurality of convex lenses 51b. The plate member 51a is arranged on a surface parallel to the light receiving surface 41a. The convex lenses 51b are regularly arranged on a surface opposite to the plate member 51a and facing to the light receiving surface 41a. With this, the microlens 51 functions as a lens array which includes a plurality of lenses. Preferably, each of the convex lenses 51b is optically masked respectively so as to prevent imaging permeated light from being affected by non-imaging permeated light. To be specific, chromium oxide is vapor-deposited on a portion of the microlens 51 where the convex lenses 51b are not formed. With this, it suppresses stray light. That is, as illustrated in FIG. 4B, the microlens 51 includes a stray light preventer 51c to prevent the plurality of convex lenses 51b from guiding undesired light to the image pickup element 41.

Although the lens array of the above-mentioned embodiment is configured by integrally forming the plate member 51a and convex lenses 51b with the glass member, it may be configured by separately arranging the plate member 51a and convex lenses 51b and fixing them to each other by, for example, an adhesive.

In regards to the rear lens group 33, the microlens 51 is preferably disposed at a position conjugate optically to an aperture stop S. That is, by schematically assuming the imaging optical system as a single lens, the microlens 51 is preferably disposed at a focal point of this single lens.

The lens holding member 52 includes a lens holding part 52a to hold the microlens 51. The lens holding member 52 is inserted into and fixed to the housing 10. The lens holding member 52 also includes a projection part 53 projecting toward the adjuster 60 and protector 54 projecting toward the light receiving surface 41a at the end of the microlens side.

The image pickup element 41 is an image sensor configured by disposing a CCD on the light-receiving surface 41a to acquire image information from the incident luminous flux. Here, the CCD is a photodetector array. The photodetector array is configured by arranging a plurality of photodiodes (photodetectors) two-dimensionally and is disposed on the image pickup element 41. The image pickup element 41 converts the information, such as intensity of the light incident to the light receiving surface 41a, into electrical signals. Note that the image pickup element 41 may be configured with a CMOS sensor or the like to acquire the image information. The supporting member 42 is disposed on the back surface of the image pickup element 41 (i.e., +Z direction side) to support the image pickup element 41 and is a ceramic-made package member.

As described later, the adjuster 60 is fixed to adjust a gap C between the microlens 51 and light receiving surface 41a by connecting and positioning the supporting member 42 and the lens holding member 52. The adjuster 60 includes an adjuster support 61 and a positioning member 62. The adjuster support 61 is provided in parallel to Z direction at one end of the adjuster 60, specifically at the supporting member side (i.e., +Z direction side). The positioning member 62 is provided in parallel to the light receiving surface 41a at the other end of the adjuster 60, specifically at the lens holding member side (i.e., −Z direction side). The adjuster support 61 has a rectangular tubular shape. The positioning member 62 has a convex shape and provided at the end of the adjuster support 61. The adjuster 60 is fixed to the supporting member 42 by the adjuster support 61 and the positioning member 62 so as to surround the image pickup element 41. The adjuster 60 further includes a first fixing part 62a and a second fixing part 61a. Here, the first fixing part 62a is an abutting surface of the positioning member 62 and lens holding member 52. The second fixing part 61a is an abutting surface of the adjuster support 61 and supporting member 42. Note that the adjuster support 61 may have a cylindrical shape instead of the rectangular tubular shape. Further, the adjuster support 61 may be configured by a pair of adjuster supports symmetrically provided with the optical axis of the image pickup element 41 so as to fix the lens holding member 52 from both sides.

The controller 90 analyzes and combines the image information acquired from the luminous flux incident to the light receiving surface 41a in accordance with program stored in a main memory (storage). With this, the controller 90 analyzes a color component corresponding to each part on the light receiving surface 41a.

Next, a movement of the color measuring camera 100 when photographing an image will be described. The luminous flux emitted from the object is incident into the optical filter 31 through the front lens group 32. Depending on the positions of the luminous fluxes, the optical filter 31 transmits the luminous fluxes in the predetermined frequencies of the corresponding color filters 31A, 31B, and 31C. That is, when the luminous fluxes pass through the optical filter 31, color information of the corresponding color filters 31A, 31B, and 31C is added to the luminous fluxes. The luminous fluxes with the color information then pass through the microlens 51 through the rear lens group 33 and are imaged on the light receiving surface 41a. The controller 90 stores the image information of the luminous fluxes with the respective color information.

The controller 90 classifies the luminous fluxes based on the color components of the color filters 31A, 31B, 31C, measures the luminance of each color component, and executes image processing such as integration processing, averaging processing, and normalization processing to distinguish the luminous fluxes passed through the color filters 31A, 31B, 31C. To be more specific, the light receiving surface 41a is an array each having a specific area, and the controller 90 extracts single color from each area. Here, the resolution of the final image is determined by the number of the convex lenses 51b. Therefore, the resolution can be increased by increasing the number of the convex lenses 51b. Accordingly, the controller 90 acquires two-dimensional spectrum information from one image by reconstructing the classified luminous fluxes into an image.

As mentioned above, the color measuring camera 100 obtains the spectrum by calculating an area of each color in the image projected onto the light receiving surface 41a from the microlens 51. In such a case, the accuracy of the size and position of the projected image have a great impact on the accuracy of the color measuring camera 100. When the focal point of the microlens 51 and the light receiving surface 41a shift to Z direction, the projected images may overlap with each other or the projected images may become too small to secure the desired number of pixels. When the focal point of the microlens 51 and the light receiving surface 41a shift to X direction or Y direction, the position of the projected images are shifted and the accuracy of the color measuring camera 100 may be deteriorated. Therefore, it is preferable to suppress the allowance to be about ±15 μm when the distance between the light receiving surface (imaging surface) 41a and the microlens 51 is designed to be 700 μm.

In this embodiment, the lens holding part 52a is disposed at a position between the first fixing part 62a and second fixing part 61a in Z direction orthogonal to the light receiving surface 41a. This will be explained in detail.

Figure 5:
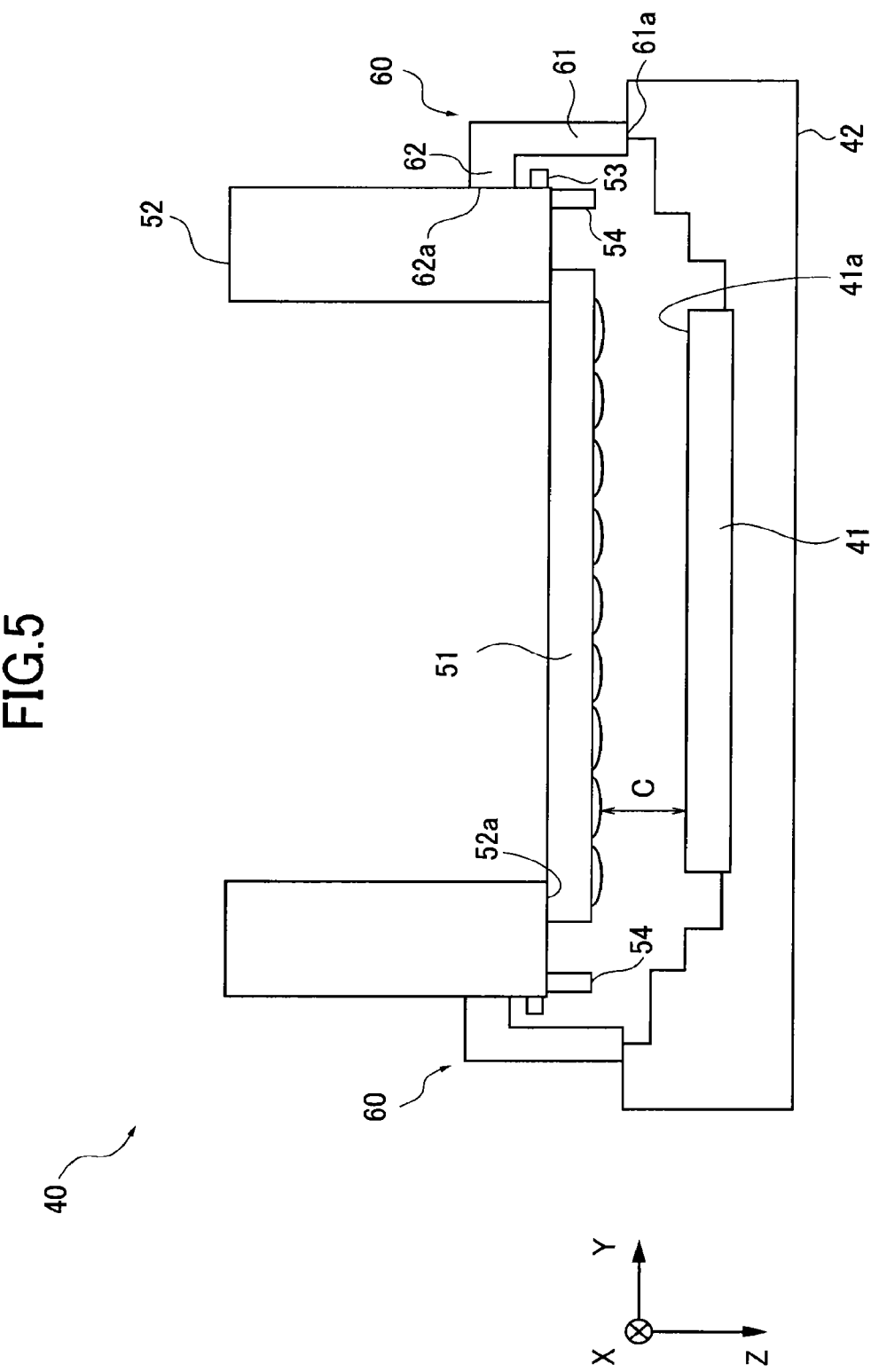
FIG. 5 is a view illustrating an example of a movement of a microlens substrate when the microlens is fixed.

In an initial state, the positioning member 62 is engaged with the projection part 53 and the image pickup element 41 is supported by the supporting member 42. In the initial state, the lens holding member 52 and microlens 51 are fixed by adhesive at the lens holding part 52a, and the adjuster 60 and the projection part 53 are engaged with each other but not fixed thereto. That is, the projection part 53 functions as an engaging part to engage with the positioning member 62. When the microlens 51, lens holding member 52, and adjuster 60 are integrally moved toward Z direction from the initial state, the adjuster support 61 abuts to the supporting member 42. The adjuster 60 is then temporally fixed by using a jig, as illustrated in FIG. 5. This state is called a temporally fixation state. In the temporally fixation state, the positioning member 62 and the lens holding member 52 are not fixed to each other, and therefore, the gap C between the microlens 51 and light receiving surface 41a is adjustable. The projection part 53 functions as a fall preventer to prevent falling of the lens holding member 52 even when force toward −Z direction is applied to the lens holding member 52.

By having the above configuration, it prevents the lens holding member 52 from coming off the adjuster 60 by engaging the projection part 53 and the positioning member 62 even when the force toward −Z direction is applied to the lens holding member 52 or/and the microlens 51.

Besides, the lens holding member 52 includes the protector 54 projecting toward the light receiving surface 41a at the end of the microlens side. With this, it prevents a collision of the microlens 51 with the image pickup element 41 and wiring (e.g., wire bonding) around the image pickup element 41 caused by a drop of the microlens 51 even when force toward +Z direction is applied to the lens holding member 52 or/and the microlens 51.

As illustrated in FIG. 5, the lens holding member 52 is supported to be movable in Z direction while abutting the side surface thereof to the end of the positioning member 62. That is, the gap C between the light receiving surface 41a and microlens 51 is freely adjustable. For instance, the gap C may be adjusted accurately by irradiating a laser beam from −Z direction side of the microlens 51 to the light receiving surface 41a and calculating a light receiving area projected on the light receiving surface 41a. Further, the gap C is adjustable regardless of the lengths of the lens holding member 52 and the adjuster 60. That is, it does not require fine adjustment using a spacer, resulting in reducing the cost. Note that a method of the positioning the lenses should not be limited to the above-mentioned method. For instance, the positioning may be adjusted by determining the positions of four corners of the microlens 51 using a laser interferometer.

After performing the positioning (i.e., after adjusting and determining the gap C), the positioning member 62 and lens holding member 52 are fixed by the adhesive at the first fixing part 62a and the adjuster support 61 and supporting member 42 are fixed at the second fixing part 61a. That is, the microlens unit 40 is in a fixed state. Since the lens holding member 52 abuts to and is fixed to the adjuster 60 at the side surface of the lens holding member 52, the first fixing part 62a is positioned on −Z direction side with respect to the lens holding part 52a. Specifically, the lens holding part 52a to hold the microlens 51 is positioned between the first fixing part 62a and the second fixing part 61a in Z direction orthogonal to the light receiving surface 41a.

Figure 7:
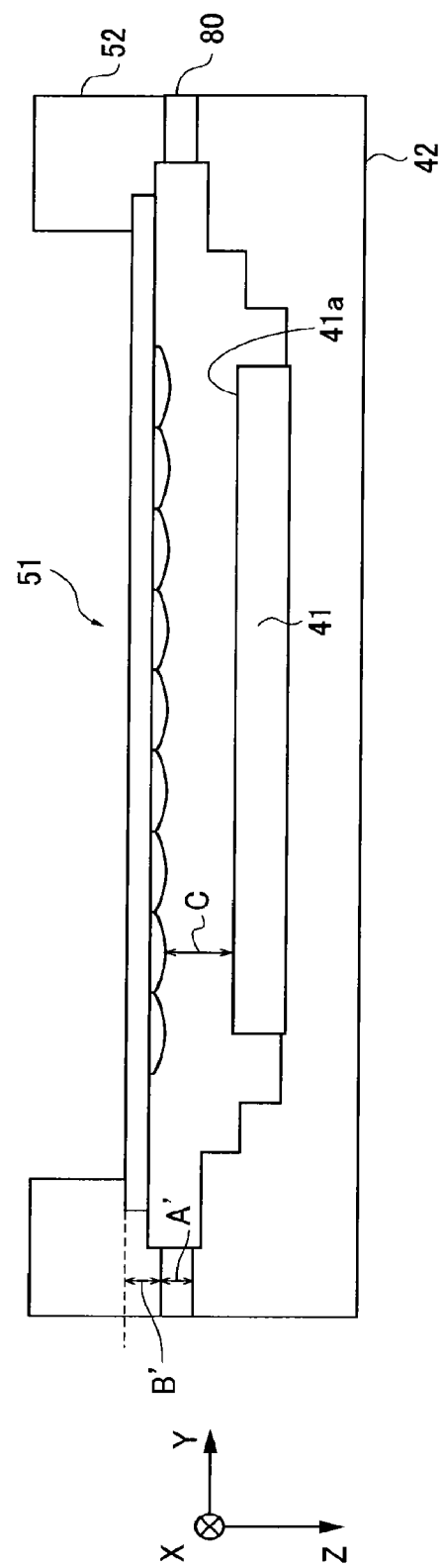
FIG. 7 is a view illustrating a configuration of a conventional microlens substrate.

As illustrated in FIG. 7, a conventional microlens unit (microlens substrate) includes a fixing member 80 between the lens holding member 52 and the supporting member 42. Here, a variation amount Δc' of the members caused by thermal expansion/compression with a temperature change Δt after the fixation in the conventional microlens unit of FIG. 7 is calculated. Note that the supporting member 42 and microlens 51 generally have relatively a small linear expansion coefficient such that variation amounts of these members are excluded from the calculation. In the following calculation, β represents a linear expansion coefficient of the lens holding member 52, γ represents a linear expansion coefficient of the fixing member 80, A' represents a distance between both ends of the fixing member 80, and B' represents a distance in Z direction from the fixing member 80 to the fixed position of the lens holding member 52 and microlens 51. Accordingly, the variation amount Δc' is expressed as: $\Delta c'=(A'\times\gamma)+(B'\times\beta)$. This means, the variation amount Δc' in the conventional microlens unit caused by the thermal expansion is a sum of the thermal expansion amounts of the fixing member 80 and the lens holding member 52. Therefore, it is difficult to reduce the variation amount in the conventional microlens unit caused by thermal expansion by simply arranging the linear expansion coefficients of materials.

Here, in the first embodiment of this disclosure, a variation amount Δc of the gap C between the light receiving surface 41a and microlens 51 caused by thermal expansion/compression with a temperature change Δt after the fixation is calculated, as illustrated in FIG. 5. Contrary to the conventional microlens unit, the variation amount Δc of the first embodiment caused by thermal expansion is calculated by subtracting a variation amount $\Delta c_{52}$ of the lens holding member 52 from a variation amount $\Delta c_{60}$ of the adjuster 60. To be specific, by disposing the fixed position of the microlens 51 at a position apart from the light receiving surface 41a, it reduces the variation of the gap C between the microlens 51 and image pickup element 41 caused by thermal expansion/compression. Additionally, by having such a configuration, the gap C between the microlens 51 and image pickup element 41 is accurately fixed.

In the first embodiment of this disclosure, the adjuster 60 is fixed to the supporting member 42 at one end and fixed to the lens holding member 52 at the other end. With this, it reduces the variation of the gap C between the microlens 51 and image pickup element 41 caused by thermal expansion/compression.

Further, in the first embodiment of this disclosure, the adjuster 60 includes the adjuster support 61 extending along the Z direction orthogonal to the light receiving surface 41a and the positioning member 62 extending parallel to the light receiving surface 41a. With this, it reduces the variation of the gap C between the microlens 51 and image pickup element 41 caused by thermal expansion/compression. Additionally, since the adjuster 60 abuts to and is fixed to the lens holding member 52, the gap C between the microlens 51 and image pickup element 41 is accurately fixed.

Further, in the first embodiment of this disclosure, the lens holding member 52 includes the projection part 53 projecting toward the adjuster side. With this, the projection part 53 prevents the lens holding member 52 from coming off the adjuster 60 by engaging with the positioning member 62. Note that in the above embodiment, the projection part 53 is configured to engage with the positioning member 62. However, the projection part 53 may be configured to engage with a side surface of the adjuster 60 when the adjuster 60 does not include the positioning member 62.

Second Embodiment

Figure 6:
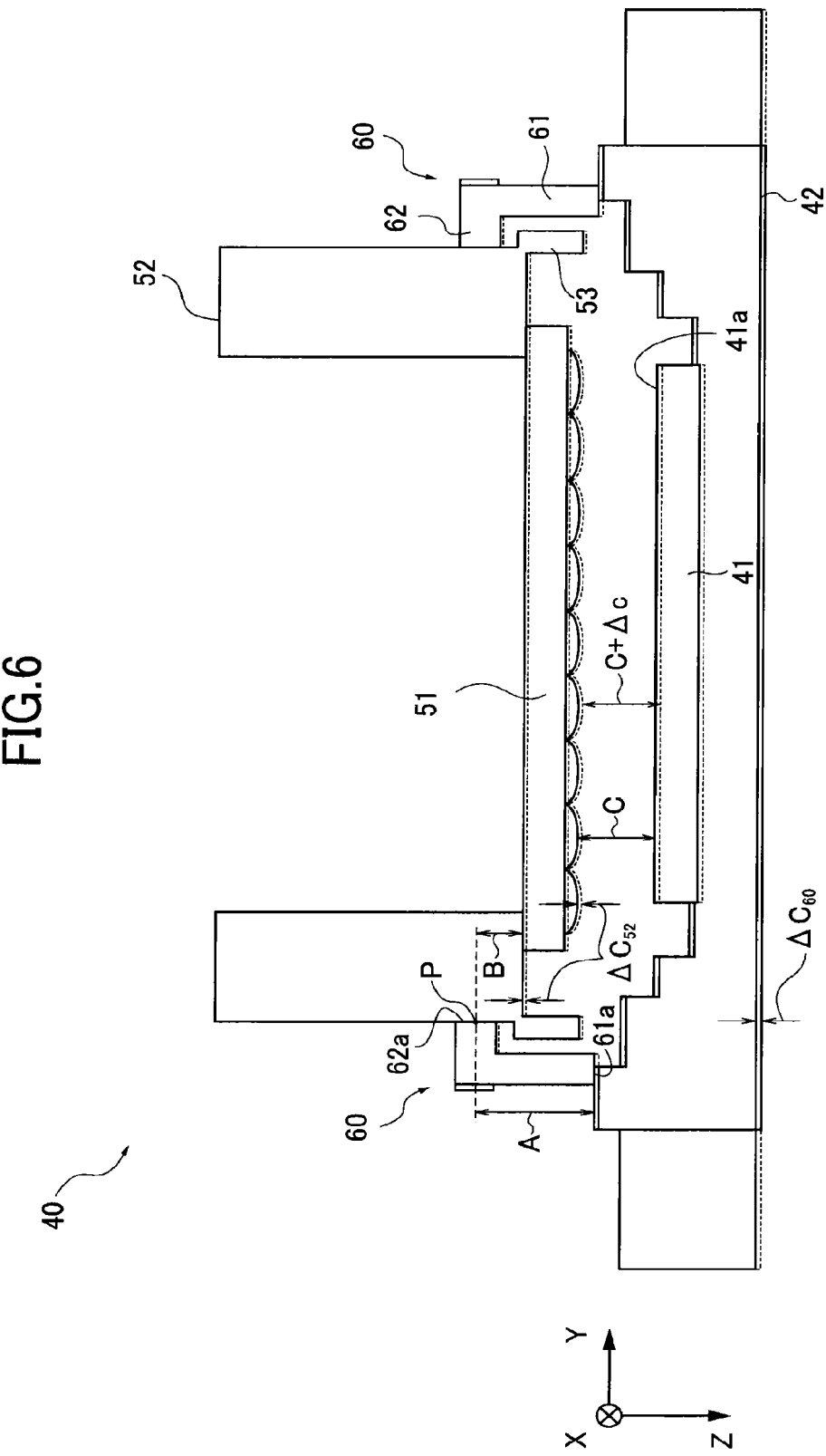
FIG. 6 is a view illustrating another example of a configuration of a microlens substrate according to a second embodiment.

FIG. 6 illustrates a configuration of a second embodiment of this disclosure. In FIG. 6, the same components as that of the first embodiment are indicated by the same reference signs and detailed explanation thereof is omitted. To facilitate calculations, the center position of the first fixing part 62a is considered as a connection point P, and the following calculations are made on the basis of the connection point P.

In the fixation state of the microlens unit 40 illustrated in FIG. 6, $\alpha$ represents a linear expansion coefficient of the adjuster 60, and A represents a distance from the connection point P to the supporting member 42 (i.e., the distance from the connection point P to the second fixing part 61a in Z direction). Further, B represents a distance from the connection point P to the fixed position of the lens holding member 52 and microlens 51 (i.e., the distance from the connection point P to the lens holding part 52a in Z direction), and $\beta$ represents a linear expansion coefficient of the lens holding member 52. Here, a ratio of A:B is directly inverse to a ratio of the linear expansion coefficient of the adjuster 60 to the linear expansion coefficient of the lens holding member 52 (i.e., the ratio of $\alpha$:$\beta$). Therefore, A:B=$\beta$:$\alpha$.

Here, a variation amount $\Delta c$ of the gap C caused by thermal expansion/compression with temperature change $\Delta t$ is calculated. The variation amount of the adjuster 60 caused by a temperature change $\Delta t$ is expressed as: $\Delta c_{60}=A\times\alpha\times\Delta t$, and the variation amount of the lens holding member 52 caused by the same is expressed as: $\Delta c_{52}=B\times\beta\times\Delta t$. As described above, the linear expansion coefficients $\alpha$, $\beta$ and the distances A, B are expressed by A:B=$\beta$:$\alpha$. Thus, the above relationships are expressed as A×$\alpha$=B×$\beta$, and therefore, $\Delta c_{60}=\Delta c_{52}$. Since each of the variation amounts $\Delta c_{60}$, $\Delta c_{52}$ of the adjuster 60 and lens holding member 52 changes on the basis of the connection point P, a change of the position of the microlens 51 is cancelled. As a result, the variation amount $\Delta c$ of the gap C becomes 0.

As mentioned above, the microlens unit 40 of the second embodiment reduces the variation amount of the gap C between the microlens 51 and image pickup element 41 caused by thermal expansion/compression. Besides, the gap C between the microlens 51 and image pickup element 41 is accurately fixed.

In the second embodiment, when the connection point P is set such that the distance A becomes greater than the distance B (i.e., A>B), the materials of the adjuster 60 and lens holding member 52 are selected such that the linear expansion coefficient $\alpha$ of the adjuster 60 becomes less than the linear expansion coefficient $\beta$ of the lens holding member 52 (i.e., $\alpha<\beta$). As described, the variation amounts $\Delta c_{60}$, $\Delta c_{52}$ of the adjuster 60 and lens holding member 52 changes on the basis of the connection point P. Therefore, the change amount $\Delta c$ of the gap C is cancelled. Consequently, it reduces the variation of the gap C between the microlens 51 and image pickup element 41 caused by thermal expansion/compression. Additionally, the gap C between the microlens 51 and image pickup element 41 is accurately fixed. Note that the connection point P in the second embodiment is set to the center of the first fixing part 62a. However, this is only an example. The connection point P is a virtual point used as the basis of the thermal expansion and may be set at another position of the first fixing part 62a.

As described above, in the embodiments of this disclosure, it reduces a variation of the gap between the microlens array and the image pickup element caused by thermal expansion and thermal compression by disposing the fixed position of the microlens array at a position apart from the light receiving surface.

Although the present invention has been described in terms of exemplary embodiments, it is not limited thereto. It should be appreciated that variations or modifications may be made in the embodiments described by persons skilled in the art without departing from the scope of the present invention as defined by the following claims.

For instance, in the temporally fixation state, the adjuster is temporally fixed to the supporting member using the jig to perform the positioning. However, the positioning member may be engaged with the lens holding member while performing the positioning.

Further, the positioning may be performed by supporting the lens supporting member using a jig with six degrees of freedom (X direction, Y direction, Z direction, and rotational directions of the corresponding directions).

The effects of the above-mentioned embodiments are only preferable effects of this disclosure, and therefore, should not be limited thereto.

What is claimed is:
1. A microlens substrate, comprising:
a light receiving section that includes a light receiving surface configured to receive light;
a supporting member that fixes the light receiving section;
a microlens array that includes a plurality of microlenses configured to guide the light to the light receiving section;
a lens holding member that holds the microlens array; and
a fixing member that fixes the supporting member and the lens holding member, wherein
the fixing member includes a first fixing part that fixes the lens holding member and a second fixing part that fixes the supporting member,
the lens holding member includes a lens holding part that holds the microlens array, and
the lens holding part is disposed at a position between the first fixing part and the second fixing part in a direction orthogonal to the light receiving surface.

2. The microlens substrate according to claim 1, wherein the fixing member includes an adjuster support extending along the direction orthogonal to the light receiving surface and a positioning member extending in parallel to the light receiving surface.

3. The microlens substrate according to claim 1, wherein the lens holding member includes a fall preventer projecting toward the fixing member.

4. The microlens substrate according to claim 1, wherein the lens holding member includes a protector projecting toward the light receiving surface.

5. The microlens substrate according to claim 1, wherein a ratio of a distance between the first fixing part and the supporting member to a distance between the first fixing part and the microlens array is directly inverse to a ratio of a linear expansion coefficient of the fixing member to a linear expansion coefficient of the lens holding member.

6. An imaging apparatus, comprising the microlens substrate according to claim 1.

* * * * *